(12) United States Patent
Becker et al.

(10) Patent No.: US 9,458,074 B2
(45) Date of Patent: Oct. 4, 2016

(54) PROCESS FOR PRODUCING PHENOL

(71) Applicant: ExxonMobil Chemical Patents Inc., Baytown, TX (US)

(72) Inventors: Christopher L. Becker, Manhattan, KS (US); James R. Lattner, LaPorte, TX (US); Keith H. Kuechler, Friendswood, TX (US); Hari Nair, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 119 days.

(21) Appl. No.: 14/375,983

(22) PCT Filed: Dec. 4, 2012

(86) PCT No.: PCT/US2012/067769
§ 371 (c)(1),
(2) Date: Jul. 31, 2014

(87) PCT Pub. No.: WO2013/130151
PCT Pub. Date: Sep. 6, 2013

(65) Prior Publication Data
US 2015/0018583 A1    Jan. 15, 2015

Related U.S. Application Data

(60) Provisional application No. 61/604,771, filed on Feb. 29, 2012.

(30) Foreign Application Priority Data

Apr. 18, 2012    (EP) .................................... 12164541

(51) Int. Cl.
C07C 37/80    (2006.01)
C07C 2/66     (2006.01)
(Continued)

(52) U.S. Cl.
CPC ................ *C07C 37/08* (2013.01); *C07C 2/66* (2013.01); *C07C 2/74* (2013.01); *C07C 5/03* (2013.01);
(Continued)

(58) Field of Classification Search
CPC ................................ C07C 37/80; C07C 2/66
USPC ............................................. 568/798; 203/58
See application file for complete search history.

(56) References Cited

U.S. PATENT DOCUMENTS 4,021,490 A * 5/1977 Hudson .................. C07C 37/80
                                                              203/58
4,439,409 A   3/1984 Puppe et al.
(Continued)

FOREIGN PATENT DOCUMENTS

EP          0 293 032     11/1988
WO          WO 97/17290    5/1997
(Continued)

*Primary Examiner* — Kamal Saeed
*Assistant Examiner* — Janet L Coppins
(74) *Attorney, Agent, or Firm* — Stephen A. Baehl

(57) ABSTRACT

In a process for producing phenol, benzene is reacted with a source of hydrogen containing methane in the presence of a hydroalkylation catalyst under conditions effective to produce a hydroalkylation reaction effluent comprising cyclohexylbenzene, benzene, hydrogen, and methane. A first stream comprising hydrogen, methane, and benzene is removed from the hydroalkylation reaction effluent and the first stream is washed with a second stream containing cyclohexylbenzene to produce a benzene-depleted hydrogen stream containing hydrogen and methane and a wash stream containing cyclohexylbenzene and benzene.

25 Claims, 1 Drawing Sheet

(51) Int. Cl.
*C07C 37/08* (2006.01)
*C07C 45/53* (2006.01)
*C07C 2/74* (2006.01)
*C07C 407/00* (2006.01)
*C07C 5/03* (2006.01)
*C07C 7/11* (2006.01)

(52) U.S. Cl.
CPC ............. *C07C 7/11* (2013.01); *C07C 37/80* (2013.01); *C07C 45/53* (2013.01); *C07C 407/00* (2013.01); *C07C 2101/14* (2013.01)

(56) References Cited

U.S. PATENT DOCUMENTS

| | | |
|---|---|---|
| 4,826,667 A | 5/1989 | Zones et al. |
| 4,954,325 A | 9/1990 | Rubin et al. |
| 5,236,575 A | 8/1993 | Bennett et al. |
| 5,250,277 A | 10/1993 | Kresge et al. |
| 5,362,697 A | 11/1994 | Fung et al. |
| 6,037,513 A | 3/2000 | Chang et al. |
| 6,049,018 A | 4/2000 | Calabro et al. |
| 6,077,498 A | 6/2000 | Diaz Cabañas et al. |
| 6,720,462 B2 | 4/2004 | Kuhnle et al. |
| 6,756,030 B1 | 6/2004 | Rohde et al. |

FOREIGN PATENT DOCUMENTS

| | | |
|---|---|---|
| WO | WO 2009/025939 | 2/2009 |
| WO | 2009/102517 | 8/2009 |

* cited by examiner

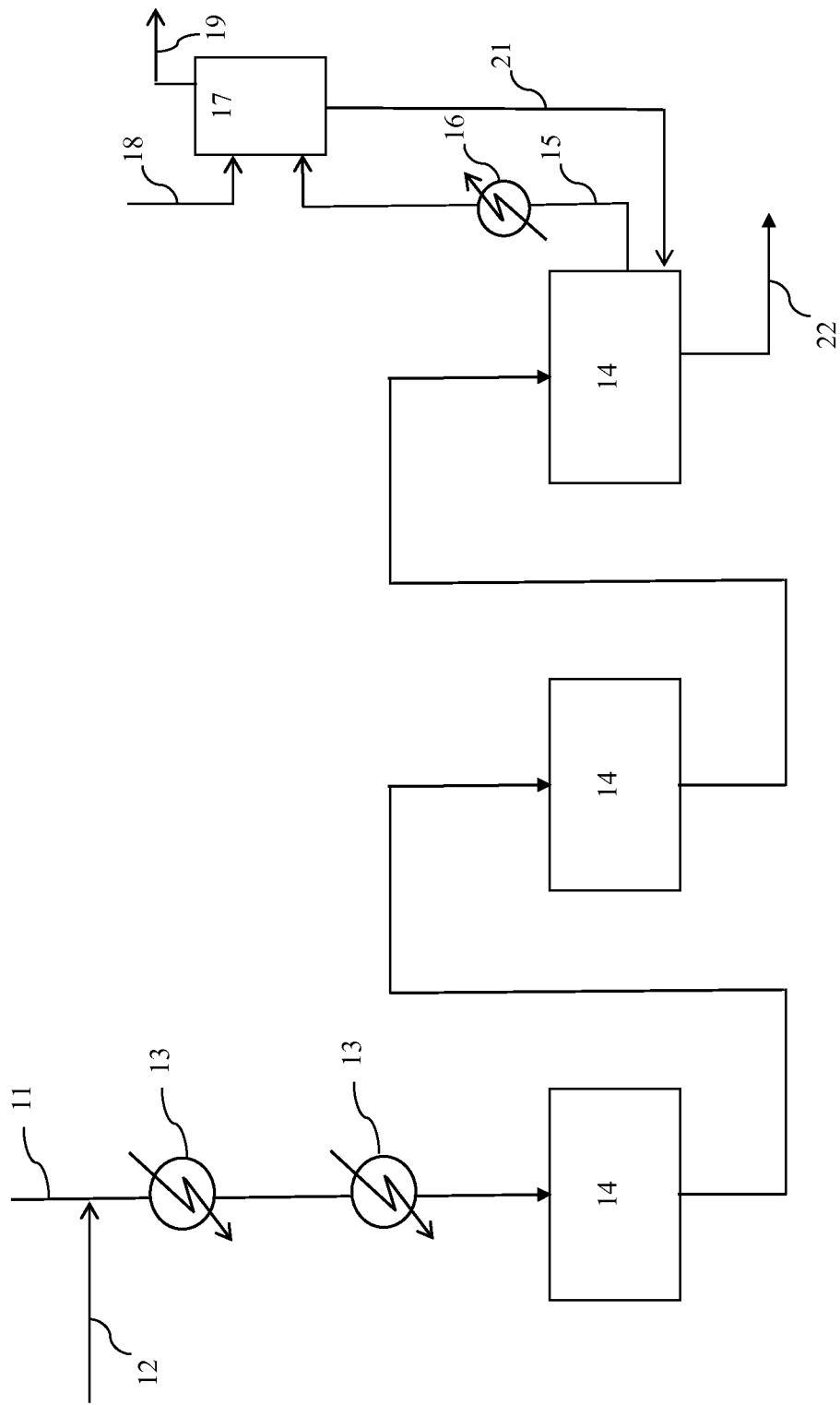

PROCESS FOR PRODUCING PHENOL

PRIORITY CLAIM TO RELATED APPLICATIONS

This application is a National Stage Application of International Application No. PCT/US2012/067769 filed Dec. 4, 2012, which claims priority to U.S. Provisional Application Ser. No. 61/604,771 filed Feb. 29, 2012 and European Application No. 12164541.0 filed Apr. 18, 2012, the disclosures of which are fully incorporated herein by their reference.

FIELD

The present invention relates to a process for producing phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, due to a developing shortage, the cost of propylene is likely to increase. Thus, a process that uses higher alkenes instead of propylene as feed and co-produces higher ketones, rather than acetone, may be an attractive alternative route to the production of phenols.

One such process proceeds via cyclohexylbenzene, followed by the oxidation of the cyclohexylbenzene to cyclohexylbenzene hydroperoxide, which is then cleaved to produce phenol and cyclohexanone in substantially equimolar amounts Although various methods are available for the production of cyclohexylbenzene, a preferred route is disclosed in U.S. Pat. No. 6,037,513, in which the cyclohexylbenzene is produced by hydroalkylating benzene with hydrogen in the presence of a bifunctional catalyst comprising a molecular sieve of the MCM-22 family and at least one hydrogenation metal selected from palladium, ruthenium, nickel, cobalt and mixtures thereof. The '513 patent also discloses that the resultant cyclohexylbenzene can be oxidized to the corresponding hydroperoxide and then decomposed to the desired phenol and cyclohexanone co-product.

One of the problems associated with producing cyclohexylbenzene by hydroalkylation of benzene is that economically viable commercial sources of hydrogen contain inert materials, such as methane, nitrogen, ethane, and propane. Being inert, these materials do not participate in the hydroalkylation reaction but, as hydrogen is consumed, they build up and must be purged. However, direct purging from, for example, the unreacted hydrogen recycle line to the hydroalkylation reactor also vents expensive hydrogen. Moreover, such a purge gas would contain benzene that would have to be removed before the purge could be vented to atmosphere.

There is therefore a need for an inexpensive process for removing inerts from the hydrogen recycle streams employed in the hydroalkylation of benzene, which method minimizes loss of useful hydrogen and benzene. The present invention seeks to provide such a process.

SUMMARY

In one aspect, the invention resides in a process for producing phenol, the process comprising:

(a) reacting benzene with a hydrogen-containing stream in the presence of a hydroalkylation catalyst under conditions effective to produce a hydroalkylation reaction effluent comprising cyclohexylbenzene, benzene, and hydrogen;

(b) removing a first stream from the hydroalkylation reaction effluent, said first stream comprising hydrogen and benzene; and (c) washing at least a portion of the first stream with a second stream containing cyclohexylbenzene to produce a benzene-depleted hydrogen stream and a wash stream containing cyclohexylbenzene and benzene.

In one embodiment, the reacting (a) is conducted in a plurality of hydroalkylation reactors connected in series and the gas stream is removed from effluent from the final hydroalkylation reactor.

Generally, the gas stream is cooled prior to the washing (c) such that the washing (c) is conducted at a temperature of about 10° C. to about 180° C., for example about 40° C. to about 160° C. In one embodiment, the gas stream flows countercurrent to said second stream in said washing (c).

In one embodiment, the cyclohexylbenzene in the second stream is produced by the reacting (a). Typically, the second stream contains less than 1 wt % benzene, or less than 10 wppm of benzene.

In one embodiment, the benzene-depleted hydrogen stream contains less than 0.01 wt % benzene.

Conveniently, the wash stream is recycled to the reacting (a).

Conveniently, the reacting (a) produces olefinic by-products in addition to cyclohexylbenzene and the process further includes the steps of:

(d) separating an impure product stream comprising cyclohexylbenzene and olefinic by-products from said hydroalkylation reaction effluent;

(e) contacting said impure product stream with said benzene-depleted hydrogen stream in the presence of a hydrogenation catalyst under conditions such that hydrogen in the benzene-depleted hydrogen stream reacts with said olefinic by-products to produce a hydrogenated product stream and a hydrogen-depleted gas stream; and (f) purging said hydrogen-depleted gas stream from the process.

Generally, the hydrogenation catalyst comprises a hydrogenation component and a support.

Typically, the hydrogenation component comprises at least one metal component selected from Groups 6 to 10 of the Periodic Table of Elements, such as palladium, and is present in amount of about 0.1 wt % to about 10 wt % based upon total weight of the hydrogenation catalyst.

Generally, the support comprises at least one of aluminum oxide, silica, silicate, aluminosilicate, carbon, and a carbon nanotube.

Conveniently, the hydrogenation conditions comprise a temperature of about 10° C. to about 200° C. and a pressure of about 100 kPa,g to about 3450 kPa,g.

In another aspect, the invention resides in a process for producing phenol, the process comprising:

(a) reacting benzene with a source of hydrogen containing methane in the presence of a hydroalkylation catalyst under conditions effective to produce a hydroalkylation reaction effluent comprising cyclohexylbenzene, benzene, hydrogen, and at least one olefinic byproduct;

(b) removing a first stream from the hydroalkylation reaction effluent, said first stream comprising hydrogen, methane, and benzene;

(c) washing the first stream with a cyclohexylbenzene-containing stream to produce a benzene-depleted stream containing hydrogen and methane and a wash stream containing cyclohexylbenzene and benzene;

(d) removing a second stream from the hydroalkylation reaction effluent, said second stream comprising at least a portion of the cyclohexylbenzene and the at least one olefinic by-product;

(e) contacting said second stream with said benzene-depleted stream in the presence of a hydrogenation catalyst under conditions such that at least a portion of the hydrogen in the benzene-depleted stream reacts with the at least one olefinic by-product to produce a hydrogenated product stream and a hydrogen-depleted gas stream containing methane; and (f) purging said hydrogen-depleted gas stream from the process.

BRIEF DESCRIPTION OF THE DRAWINGS

FIG. 1 is a schematic drawing of part of an integrated process for producing phenol from benzene according to one embodiment of the invention.

DETAILED DESCRIPTION OF THE EMBODIMENTS

Described herein is a process for producing phenol from benzene in which the benzene is initially hydroalkylated to produce cyclohexylbenzene and the cyclohexylbenzene may be oxidized to produce cyclohexylbenzene hydroperoxide, which is subsequently cleaved to produce phenol and cyclohexanone. The product of the hydroalkylation step typically contains benzene and hydrogen which must be recycled to ensure satisfactory process economics. As such, methods for improving the recovery of such benzene and hydrogen are desired.

Additionally, as indicated above commercial hydrogen sources always contain small amounts of inert materials which, if not purged, will build up in these recycle streams. Direct purging to atmosphere is not a viable option since the purge gas inherently contains benzene. Thus, the present process provides an integrated process for producing phenol via the hydroalkylation of benzene wherein inexpensive and environmentally friendly process is provided for removing inerts with minimal loss of valuable reagents and products.

Production of the Cyclohexylbenzene

One step of an integrated process for producing phenol is the selective hydrogenation of benzene in the presence of a bifunctional hydroalkylation catalyst. The hydroalkylation reaction produces cyclohexylbenzene (CHB) according to the following reaction:

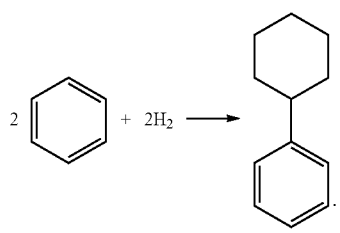 [SMILES: c1ccccc1 ; c1ccc(C2CCCCC2)cc1]

Any commercially available benzene feed can be used in the hydroalkylation reaction, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen. Generally, the hydrogen feed will contain inert materials, such as methane, nitrogen, ethane, and propane. In this respect, the term "inert material" is used to mean components typically found in a commercial hydrogen feed that do not participate in the hydroalkylation reaction.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically, the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439, 409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56, and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27, (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite or anauxite. Such clays can be used in the raw state as originally mined or initially subjected to calcination, acid treatment, or chemical modification. Suitable metal oxide binders include silica, alumina, zirconia, titania, silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Treatment of the Cyclohexylbenzene Product

Although the hydroalkylation reaction using an MCM-22 family zeolite catalyst is highly selective towards cyclohexylbenzene, the hydroalkylation reaction will inevitably produce certain by-products. As stated previously, a prevalent by-product is normally cyclohexane but generally the reaction effluent will also contain dicyclohexylbenzene, tricyclobenzene and even heavier alkylates, as well as methylcyclopentane and certain olefins, such as cyclohexene, phenyl cyclohexene methylcyclopentene, and methylcyclopentenylbenzene. The reaction effluent will also contain benzene and hydrogen, together with the inert components introduced with the hydrogen feed.

To recover the various components, the hydroalkylation reaction effluent is normally fractionated to separate the effluent into one or more $C_6$ fractions containing most of the benzene and most of the cyclohexane and methylcyclopentane by-products, a $C_{12}$ fraction containing most of the cyclohexylbenzene product, and a $C_{18}$ fraction containing most of the dicyclohexylbenzene by-product, and possibly a $C_{24}$ or higher product heavy alkylate byproduct.

In one embodiment, the fractionation of the hydroalkylation reaction effluent produces a single $C_6$ fraction and this $C_6$ fraction is then contacted with a dehydrogenation catalyst under dehydrogenation conditions sufficient to convert at least a portion of the cyclohexane in the $C_6$ fraction to benzene but change the amount of methylcyclopentane by no more than 10% of the total amount of the $C_6$ fraction contacted with the dehydrogenation catalyst, said amounts on a weight basis. Generally, the dehydrogenation is arranged to convert at least 25 wt %, such at least 50 wt %, for example at least 90 wt % of the cyclohexane in the $C_6$ fraction to benzene but change the amount of methylcyclopentane by no more 5 wt %, such as no more than 2 wt %, or no more than 1 wt %, or no more than 0.5 wt %, or no more than 0.1 wt % of the total amount of the $C_6$ fraction contacted with the dehydrogenation catalyst. A suitable catalyst to effect the desired dehydrogenation comprises an inorganic support comprising 0.05 wt % to 0.5 wt % of a metal selected from Group 14 of the Periodic Table of Elements; such as tin, and 0.1 wt % to 2 wt % of a metal selected from Groups 6 to 10 of the Periodic Table of Elements, such as platinum and/or palladium, the wt % s being based upon total weight of the first catalyst. Conveniently, the support is selected from the group consisting of silica, a silicate, an aluminosilicate, zirconia, and carbon nanotubes, and preferably comprises silica. Suitable dehydrogenation conditions include a temperature of about 250° C. to about 500° C., a pressure of about 100 kPa to 7000 kPa, a weight hourly space velocity of about 0.2 $hr^{-1}$ to 50 $hr^{-1}$, and a hydrogen to hydrocarbon feed molar ratio of about 0 to about 20.

After removal of the hydrogen, the dehydrogenation effluent typically contains at least 25 wt %, such at least 50 wt %, for example at least 90 wt % benzene, from about 0.1 wt % to about 10 wt %, such as from about 1 wt % to about 5 wt %, cyclohexane and from about 0.1 wt % to about 5 wt %, such as from about 0.5 wt % to about 1 wt %, methylcyclopentane. The dehydrogenation effluent is then fractionated to produce a major fraction rich in benzene and a minor fraction rich in methylcyclopentane. The benzene-rich fraction typically comprises from about 90 wt % to about 99 wt % of the liquid dehydrogenation effluent and contains no more than 5 wt %, normally at least 0.01 wt %, such as about 0.1 wt % to about 1 wt %, methylcyclopentane, possibly no detectable methylcyclopentane, and from about 0.1 wt % to about 10 wt % cyclohexane, such as from about 0.5 wt % to about 5 wt % cyclohexane. The methylcyclopentane-rich fraction typically comprises from about 1 wt % to about 10 wt % of the liquid dehydrogenation effluent and contains from about 5 wt % to about 50 wt % methylcyclopentane, from about 5 wt % to about 50 wt % cyclohexane and from about 10 wt % to about 80 wt % benzene. The benzene fraction is recycled to the hydroalkylation reaction, whereas the methylcyclopentane-rich fraction is normally recovered for use as a motor gasoline blendstock.

In another embodiment, the fractionation of the hydroalkylation reaction effluent produces at least two $C_6$ fractions, namely a first, methylcyclopentane containing fraction and a second, benzene-containing fraction. The first fraction typically comprises from about 1 wt % to about 10 wt % of the liquid hydroalkylation reaction effluent and contains from about 1 wt % to about 99 wt %, such as from about 2 wt % to about 80 wt %, of the methylcyclopentane contained in hydroalkylation reaction effluent. Thus, the first fraction generally contains from about 5 wt % to about 50 wt % methylcyclopentane, together with about 5 wt % to about 50 wt % cyclohexane and about 10 wt % to about 80 wt % benzene. The second fraction typically comprises from about 90 wt % to about 99 wt % of the liquid hydroalkylation effluent and contains up to 5 wt %, such as from about 0.01 wt % to about 1 wt %, methylcyclopentane, possibly no detectable methylcyclopentane, the reminder being composed mainly of benzene and cyclohexane. The second fraction is therefore subjected to the dehydrogenation reaction discussed above, while the first fraction is normally recovered for use as a motor gasoline blendstock.

As discussed above, fractionation of the hydroalkylation reaction effluent also produces a $C_{12}$ fraction containing most of the cyclohexylbenzene and a $C_{18}$ fraction containing most of the dicyclohexylbenzene. The cyclohexylbenzene is fed to the oxidation step discussed below whereas, depending on the amount of the dicyclohexylbenzene produced, it may be desirable to either (a) transalkylate the dicyclohexylbenzene with additional benzene, or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 $hr^{-1}$ to about 10 $hr^{-1}$ on total feed, and a benzene/dicyclohexylbenzene weight ratio about of 1:1 to about 5:1. The transalkylation reaction can, and typically will, generate additional methylcyclopentane.

Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia, and mixtures thereof. Generally, the acid catalyst includes at least one aluminosilicate, aluminophosphate or silicoaluminphosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

It is to be appreciated that the transalkylation and dealkylation reactions can, and typically will, generate additional methylcyclopentane and hence the products of these reactions can be subjected to the separation steps described above to generate the $C_6$ fraction(s), which may subsequently be subjected to dehydrogenation.

In addition to recovering and treating the valuable products and by-products of the hydroalkylation reaction, the present process provides a novel route for recovering valuable benzene and hydrogen and preventing the build-up of inert components in the hydrogen recycle stream of the process. Thus, a gaseous first stream containing at least some of the hydrogen in the reaction effluent, together with some entrained benzene and inert components, such as methane, is removed from the reaction effluent from the hydroalkylation reactor. In various embodiments, the hydroalkylation reaction effluent contains at least 10 mol %, or at least 15 mol %, or at least 20 mol % of at least one inert material, based upon the total number of moles in the hydroalkylation reaction effluent. The hydrolkylation reaction effluent may further comprise at least 1 mol %, or at least 5 mol %, or at least 10 mol % of the hydrogen from the hydroalkylation reaction effluent, based upon the number of moles of the hydroalkylation reaction effluent. Where the hydroalkylation reaction is conducted in a plurality of series-connected reactor, the first stream is preferably removed from the effluent from the final reactor since this has the highest concentration of inert materials.

The first stream may be fed to a wash column where the stream is contacted, preferably in countercurrent manner, with a second stream containing cyclohexylbenzene, generally in an amount in excess of 5 wt %, or 7 wt % or 10 wt % of the second stream. The cyclohexylbenzene employed second stream may be obtained from the hydroalkylation reaction but is preferably subjected to an initial benzene removal step to reduce the benzene content of the second stream to less than 1 wt %, such as less than 10 wppm.

The first stream is generally cooled before entering the wash column such that washing with the second stream is conducted at a temperature of about 10° C. to about 180° C., such as about 40° C. to about 160° C. The washing transfers benzene from the first stream to the second stream so as to produce a benzene-depleted hydrogen stream (which may also contain methane) and a wash stream containing cyclohexylbenzene and benzene. In this respect, when a composition is described as being "depleted in" a specified species (e.g., benzene-depleted), it is meant that the wt % of the specified species in that composition is depleted relative to the feed composition (i.e., the input). In other words, the benzene-depleted hydrogen stream contains less benzene than the first stream.

Generally, at least 50 wt %, or at least 60 wt %, or at least 70 wt %, or at least 80 wt %, or at least 90 wt % of the benzene contained in the first stream is transferred to the wash stream. Additionally, the wash stream may contain at least 50 wt %, or at least 60 wt %, or at least 70 wt %, or at least 80 wt % or at least 90 wt % of cyclohexylbenzene. Thus, the wash stream is composed mainly of benzene and cyclohexylbenzene and can either be recycled to the hydroalkylation step or combined with the hydroalkylation effluent and fed to the product recovery section.

The benzene-depleted hydrogen stream contains less than 0.1 wt % benzene, or less than 0.01 wt % benzene and can either be flared or more preferably, given its high hydrogen content, can be used to hydrogenate the olefins that are formed as a by-product of the hydroalkylation step. This is conveniently effected by separating from the hydroalkylation reaction effluent an impure product stream comprising cyclohexylbenzene and olefinic by-products from the hydroalkylation reaction effluent. The impure product stream is optionally combined with the wash stream, and then contacted with the benzene-depleted hydrogen stream in the presence of a hydrogenation catalyst under conditions such that hydrogen in the benzene-depleted hydrogen stream reacts with the olefinic by-products to produce a hydrogenated product stream and a hydrogen (and benzene)-depleted gas stream. The hydrogen (and benzene)-depleted gas stream may then be purged from the process (e.g., through flare).

Typically, the hydrogenation catalyst comprises a hydrogenation component and a support. Suitable hydrogenation components comprise at least one metal component selected from Groups 6 to 10 of the Periodic Table of Elements, particularly platinum, whereas suitable supports comprise at least one of aluminum oxide, silica, silicate, aluminosilicate, carbon, and a carbon nanotube. Generally, the hydrogenation catalyst comprises about 0.1 wt % to about 10 wt % of the hydrogenation component, the wt % based upon total weight of the hydrogenation catalyst. Suitable hydrogenation conditions comprise a temperature of about 10° C. to about 200° C. and a pressure of about 100 kPa,g to about 3450 kPa,g.

Cyclohexylbenzene Oxidation

In order to convert the cyclohexylbenzene into phenol and cyclohexanone, all or a portion of the cyclohexylbenzene produced in the hydroalkylation step may be oxidized to the corresponding hydroperoxide. This is accomplished by contacting the cyclohexylbenzene with an oxygen-containing gas, such as air and various derivatives of air. For example, it is possible to use air that has been compressed and filtered to remove particulates, air that has been compressed and cooled to condense and remove water, or air that has been enriched in oxygen above the natural approximately 21 mol % in air through membrane enrichment of air, cryogenic separation of air, or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Preferably, the catalyst is N-hydroxyphthalimide. Another suitable catalyst is N,N', N"-thihydroxyisocyanuric acid.

These oxidation catalysts can be used either alone or in conjunction with a free radical initiator, and further can be used as liquid-phase, homogeneous catalysts, or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent may be subjected to a cleavage reaction, with or without undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Publication No. WO 2009/025939.

Hydroperoxide Cleavage

Another reactive step in the conversion of the cyclohexylbenzene into phenol and cyclohexanone involves the acid-catalyzed cleavage of the cyclohexyl-1-phenyl-1-hydroperoxide produced in the oxidation step.

Generally, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to no greater than 3000 wppm, or at least 150 wppm to no greater than 2000 wppm of the acid catalyst, or at least 300 wppm and no greater than 1500 wppm of the acid catalyst, based upon total weight of the cleavage reaction mixture.

In other embodiments, a heterogeneous acid catalyst is employed for the cleavage reaction, such as molecular sieve, and in particular, a molecular sieve having a pore size in excess of 7 Å. Examples of suitable molecular sieves include zeolite beta, zeolite Y, zeolite X, ZSM-12, and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction, but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Generally, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage reaction mixture is completely, or predominantly, in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon 6 and nylon 6,6.

The phenol produced through the processes disclosed herein may be used, for example, to produce phenolic resins, bisphenol A, ε-caprolactam, adipic acid, and/or plasticizers.

The invention will now be more particularly described with reference to the accompanying drawings and the following non-limiting examples.

Referring to the drawings, FIG. 1 illustrates part of an integrated process for producing phenol according to a first embodiment of the invention. In this process, hydrogen from line 11 is mixed with benzene from line 12 and the resultant mixed stream is heated by heat exchangers 13 before being fed to the first of three vertically disposed, series-connected hydroalkylation reactors 14. Each of the reactors 14 contain hydroalkylation catalyst and is operated under conditions such that benzene and hydrogen in the feed react to produce cyclohexylbenzene together with the by-products discussed above.

The hydroalkylation reaction product exiting the final reactor 14 is a mixed gas/liquid phase composition composed mostly of cyclohexylbenzene, dicyclohexylbenzene, cyclohexane and benzene, and hydrogen. The product does, however, also typically contain some inert components, usually methane, present in the original hydrogen feed. A first stream from the hydroalkylation reaction product exiting the final reactor 14 is fed by line 15 through a cooler 16 to the lower end of a wash column 17, which at its upper end receives a substantially benzene-free cyclohexylbenzene stream (e.g., from a debenzenizer not shown) via line 18. Line 15 typically contains a portion of the hydroalkylation reaction product that comprises mostly hydrogen and benzene and is substantially in the vapor phase. The cyclohexylbenzene stream flows downwards through the column 17 countercurrent to the first stream and removes and adsorbs the benzene contained by the first stream in line 15. Thus, a benzene-depleted hydrogen and inert (e.g., methane) stream flows out of the top of the column 17 and is conveniently fed by line 19 to a hydrogenation reactor (not shown) where it is contacted with olefinic by-products to produce a hydrogenated product stream and a hydrogen-depleted gas stream (e.g., with a relatively high concentration of inert materials). The hydrogen-depleted gas stream may then be purged from the process.

Exiting the bottom of the column 17 is a liquid wash stream which contains cyclohexylbenzene and benzene and may be recycled by line 21 to the reaction product exiting the final reactor 14.

A second stream containing all or a portion of the remainder of the hydroalkylation reaction product, including most of the desirable cyclohexylbenzene, may exit the final reactor 14 via line 22 for later use in the process.

The invention claimed is:

1. A process for producing phenol, the process comprising:
   (a) reacting benzene with a hydrogen-containing stream in the presence of a hydroalkylation catalyst under conditions effective to produce a hydroalkylation reaction effluent comprising cyclohexylbenzene, benzene, and hydrogen;
   (b) removing a first stream from the hydroalkylation reaction effluent, said first stream comprising hydrogen and benzene; and
   (c) washing at least a portion of the first stream with a second stream containing cyclohexylbenzene to produce a benzene-depleted hydrogen stream and a wash stream containing cyclohexylbenzene and benzene.

2. The process of claim 1, wherein the first stream is substantially in the vapor phase and the second stream is substantially in the liquid phase.

3. The process of claim 1, wherein at least 50 wt % of the benzene contained in said at least a portion of the first stream is transferred to the wash stream in said washing (c), the wt % based upon the weight of said at least a portion of the first stream.

4. The process of claim 1, wherein the second stream contains less than 1 wt % of benzene, based upon the weight of the second stream.

5. The process of claim 1, wherein the benzene-depleted hydrogen stream contains less than 0.1 wt % benzene, based upon the weight of the benzene-depleted hydrogen stream.

6. The process of claim 1, wherein the benzene-depleted hydrogen stream contains less than 0.01 wt % benzene, based upon the weight of the benzene-depleted hydrogen stream.

7. The process of claim 1, wherein the first stream contains at least 10 mol % of the hydrogen from the hydroalkylation reaction effluent, the mol % based upon the total moles of the hydroalkylation reaction effluent.

8. The process of claim 1, wherein the hydrogen-containing stream further comprises at least one inert material selected from methane, nitrogen, ethane, and propane, and at least a portion of the inert material is present in the hydroalkylation reaction effluent and the benzene-depleted hydrogen stream.

9. The process of claim 8, wherein at least a portion of the benzene-depleted hydrogen stream is removed from the process.

10. The process of claim 1, wherein the wash stream contains at least 80 wt % cyclohexylbenzene, based upon the weight of the wash stream.

11. The process of claim 1, wherein said reacting (a) is conducted in a plurality of hydroalkylation reactors connected in series and the first stream is removed from the hydroalkylation reaction effluent from the final hydroalkylation reactor.

12. The process of claim 1, wherein the first stream is cooled prior to the washing (c).

13. The process of claim 1, wherein the washing (c) is conducted at a temperature of about 10° C. to about 180° C.

14. The process of claim 1, wherein the washing (c) is conducted at a temperature of about 40° C. to about 160° C.

15. The process of claim 1, wherein the first stream flows countercurrent to said second stream in said washing (c).

16. The process of claim 1, wherein at least a portion of the cyclohexylbenzene contained in the second stream is produced by the reacting (a).

17. The process of claim 1, wherein at least a portion of the wash stream is recycled to the reacting (a).

18. The process of claim 1, wherein said reacting (a) produces olefinic by-products in addition to cyclohexylbenzene and the process further includes the steps of:
   (d) separating an impure product stream comprising cyclohexylbenzene and olefinic by-products from said hydroalkylation reaction effluent;
   (e) contacting said impure product stream with said benzene-depleted hydrogen stream in the presence of a hydrogenation catalyst under conditions such that hydrogen in the benzene-depleted hydrogen stream reacts with said olefinic by-products to produce a hydrogenated product stream and a hydrogen-depleted gas stream; and
   (f) purging said hydrogen-depleted gas stream from the process.

19. The process of claim 18, wherein at least a portion of the wash stream is recycled to (d).

20. The process of claim 18, wherein the hydrogenation catalyst comprises a hydrogenation component and a support.

21. The process of claim 20, wherein the hydrogenation component comprises at least one metal component selected from Groups 6 to 10 of the Periodic Table of Elements.

22. The process of claim 18, wherein the hydrogenation catalyst comprises about 0.1 wt % to about 10 wt % of the hydrogenation component, the wt % based upon total weight of the hydrogenation catalyst.

23. The process of claim 18, wherein the hydrogenation conditions comprise a temperature of about 10° C. to about 200° C. and a pressure of about 100 kPa, gauge to about 3450 kPa, gauge.

24. The process of claim 18, and further comprising:
   (g) oxidizing at least a portion of the cyclohexylbenzene in said hydrogenated product stream to cyclohexylbenzene hydroperoxide; and
   (h) cleaving at least a portion of the cyclohexylbenzene hydroperoxide produced in (g) to produce phenol and cyclohexanone.

25. A process for producing phenol, the process comprising:
   (a) reacting benzene with a source of hydrogen containing methane in the presence of a hydroalkylation catalyst under conditions effective to produce a hydroalkylation reaction effluent comprising cyclohexylbenzene, benzene, hydrogen, and at least one olefinic byproduct;
   (b) removing a vapor stream from the hydroalkylation reaction effluent, said vapor stream comprising hydrogen, methane, and benzene;
   (c) washing the vapor stream with a liquid cyclohexylbenzene-containing stream to produce a benzene-depleted stream containing hydrogen and methane and a wash stream containing cyclohexylbenzene and benzene;
   (d) removing a second stream from the hydroalkylation reaction effluent, said second stream comprising at least a portion of the cyclohexylbenzene and the at least one olefinic by-product;
   (e) contacting said second stream with said benzene-depleted stream in the presence of a hydrogenation catalyst under conditions such that at least a portion of the hydrogen in the benzene-depleted stream reacts with the at least one olefinic by-product to produce a hydrogenated product stream and a hydrogen-depleted gas stream containing methane; and
   (f) purging said hydrogen-depleted gas stream from the process.

* * * * *